(12) United States Patent
Hseu et al.

(10) Patent No.: US 6,271,003 B1
(45) Date of Patent: Aug. 7, 2001

(54) **METHOD FOR IDENTIFYING *CORDYCEPS SINENIS***

(75) Inventors: Ruey-Shyang Hseu, 3rd Floor, No.46, Lane 212, Chien Kuo S. Rd., Section 1; Chih-Shang Chen, both of Taipei (TW)

(73) Assignees: Ruey-Shyang Hseu; Soon Lo, both of Taipei; Shih-Jen Wang, Hsian, all of (TW)

( * ) Notice: Subject to any disclaimer, the term of this patent is extended or adjusted under 35 U.S.C. 154(b) by 0 days.

(21) Appl. No.: 09/333,265

(22) Filed: Jun. 15, 1999

(51) Int. Cl.⁷ .............................. C12P 19/34; C12Q 1/70; C12N 1/20; C12N 15/11
(52) U.S. Cl. .................. 435/91.2; 435/6; 435/254.1; 536/23.1
(58) Field of Search .................... 435/91.2, 6, 254.1; 536/23.1

(56) References Cited

U.S. PATENT DOCUMENTS 5,434,048 * 7/1995 Simon et al. ..................... 435/6

OTHER PUBLICATIONS

Fulton, C.E. & Brown, A.E., Use of SSU rDNA group–I intron to distinguish *Monilinia fructicola* from *M.I laxa* and *M. fructigena*, FEMS Micro. Letters 157:307–312, 1997.*

Meyers, R.A., Molecular Biology and Biotechnology, "PCR Technology" pp. 641–648, 1995.*

* cited by examiner

Primary Examiner—W. Gary Jones
Assistant Examiner—B J Forman
(74) Attorney, Agent, or Firm—Birch, Stewart, Kolasch & Birch, LLP.

(57) ABSTRACT

The present invention is drawn to a method for identifying *Cordyceps sinensis*, by amplifying a specimen's 18S rRNA polymorphism by PCR using primer pair NS3 and NS6; digesting the PCR product with restriction enzyme Cfo I; and identifying a genuine *Cordyceps sinensis* specimen by determining the presence of a PCR product digestible with the restrictions enzyme Cfo I and a DNA fragment in the polymorphism of the specimen belonging to a specific DNA fragment in the polymorphism of *Cordyceps sinensis*.

2 Claims, 1 Drawing Sheet

METHOD FOR IDENTIFYING *CORDYCEPS SINENIS*

Figure 1:
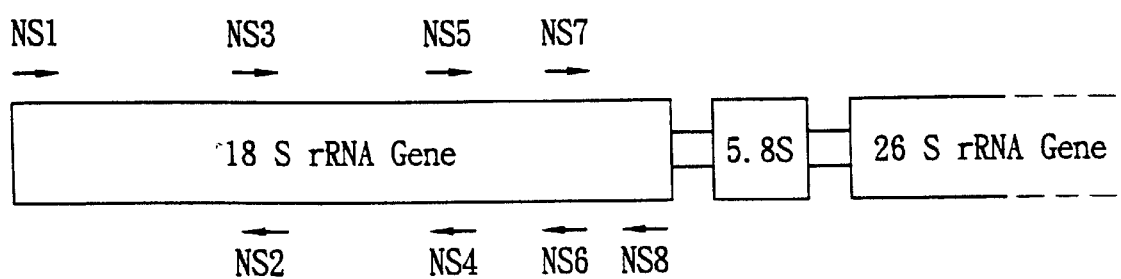

BACKGROUND OF THE INVENTION (1) Field of the Invention

The invention relates to a method for distinguishing *Cordyceps sinensis*, and more particularly to a laser level apparatus that is easy to use and has multipurpose uses.

(2) Description of the Prior Art

*Cordyceps sinensis* (*C. sinensis*) is a complex having a sclerotium and a stroma and is grown from a bug-parasitized fungus that parasitizes in a worm of hepialus armoricanus oberthur. According to the Alexopoulos classification of 1996, *C. sinensis* belongs to the Cordyceps Fr of the Clavicipiyaceae of the Clavicipitales of Ascomycetes. Currently, there are about 400 species found on the planet, which belong to the Cordyceps Fr genus. Among those species, few possess medical ingredients; such as *C. sinensis, C. sobolifera, C. militaris, C. hawkesii*, and so on. Therein, *C. sinensis* is the most popular one. After pharmacological study, *C. sinensis* was found to have active ingredients for curing tumors, kidney inflammation and aging, and for improving immunizability. Therefore, *C. sinensis* has become one of the important topics with studies of medical fumgi.

Due to the important medical potential of *C. sinensis*, healthy foods containing *C. sinensis* ingredients are popular products for health-care and age-care. However, while *C. sinensis* is widely accepted, questions arise to what *C. sinensis* really is. What are actual ingredients of a *C. sinensis*? What characteristics does a genuine *C. sinensis* have? How to identify a real *C. sinensis*? So far, no assured answer for any of the preceding questions is provided. Until now, people studying *C. sinensis* or the related Cordyceps can only work on the species collection, description, and identification. Regarding the medical potential of *C. sinensis*, "existing some metabolic products with some active ingredients for disease-prevention" is the only conclusion that can be provided. Of course, in some literatures, some efforts have been made to further understand the aspect of the Cordyceps, particularly *C. sinensis*, in view of the nature variety of the sexless Cordyceps. However, due to the collection difficulty, identification and reservation of *C. sinensis*, and also due to the difficulty in artificially cultivating the stroma, a clear picture in classification and a genuine relationship between the sex generation and the sexless generation has not been found so far. Hence, the confusion in standardizedly distinguishing *C. sinensis* is still there.

SUMMARY OF THE INVENTION

Since current classification methodologies by configuration, by physiology, or by biochemistry cannot provide a satisfactory and accurate classification of *C. sinensis*; a real *C. sinensis* can't be certainly identified. Therefore, a new method in classifying the Cordyceps is urgently needed. Accordingly, the present invention teaches a method for distinguishing *Cordyceps sinensis*. In view of gene ordering, the difference between *C. sinensis* and other Cordyceps can be determined. Further, the method of the present invention can be applied to distinguish so-called *C. sinensis* or fungi in the market or in the fungi centers. By providing the method of the present invention, specific nature characteristics for *C. sinensis* can be defined. Thereby, a standard and wide-acceptable distinguishing method for *C. sinensis* can be provided.

According to the present invention, the rRNA gene is as an operational target for the distinguishing method, in which the rRNA is the most popular gene in species classification. The rRNA has advantages in a high copy number and a high-degree conservability of evolution. The method of the present invention is first to locate the 18SrRNA of the DNA extracted from a specimen or a fungus, and then to analysis the 18SrRNA by the PCR-RFLP technique widely used in identifying fungi. By using restriction enzyme Cfo I and digesting NS3 and NS6 as the primers, it is found in the digesting polymorphism of the amplification of 18S rRNA gene that *C. sinensis* opposes a total different DNA segment to any other sinensis. This finding can be applied to distinguish *C. sinensis* from other sinensises. Also, thereby, a distinguishing method for C. sinensis can be proposed. The method for distinguishing *C. sinensis* in accordance with the present invention can then become a standard and accurate guideline of identifying *C. sinensis* to the professionals and the related bureau.

BRIEF DESCRIPTION OF THE TABLES AND DRAWINGS

The present invention will now be specified with reference to its preferred embodiments illustrated in the tables and drawings, in which Table 1 lists the source and collection number of Cordyceps specimens in this specification;

Table 2 lists the collection number of Cordyceps strains in this specification;

Table 3 lists the primers used in this specification. NS 1 =SEQ ID NO: 1. NS3 =SEQ ID NO:2. NS4 =SEQ ID NO:3. NS5 =SEQ ID NO:4. NS6 =SEQ ID NO:5.

Table 4 lists the restriction fragment sizes for amplification of Table 1 specimens' 18S rRNA gene by polymerase chain reaction (PCR) using primer pair NS1 and NS4, in which the product was further digested with restriction enzymes Hpa II, Rsa I, Hae III, Sau 3A and Cfo I;

Table 5 lists the restriction fragment sizes for amplification of Table 2 specimens' 18S rRNA gene by polymerase chain reaction (PCR) using primer pair NS1 and NS4, in which the product was further digested with restriction enzymes Hpa II, Rsa I, Hae III, Sau 3A and Cfo I;

Table 6 lists the restriction fragment sizes for amplification of Table 1 specimens' 18S rRNA gene by polymerase chain reaction (PCR) using primer pair NS3 and NS6, in which the product was further digested with restriction enzyme Cfo I;

Table 7 lists the restriction fragment sizes for amplification of Table 2 specimens' 18S rRNA gene by polymerase chain reaction (PCR) using primer pair NS3 and NS6, in which the product was further digested with restriction enzyme Cfo I; and FIG. 1 shows the locations on nuclear rDNA of PCR primers, in which the arrowhead represent the 3' end of each primer.

DESCRIPTION OF THE PREFERRED EMBODIMENT

The invention disclosed herein is directed to a method for distinguishing *Cordyceps sinensis*. In the following description, numerous details are set forth in order to provide a thorough understanding of the present invention. It will be appreciated by one skilled in the art that variations of these specific details are possible while still achieving the results of the present invention. In other instances, well-known components are not described in detail in order not to unnecessarily obscure the present invention.

To show the objectiveness of the method in accordance with the present invention, specimens for Cordyceps testing are collected from various sources. Except for *C. sinensis, C.*

*militaris* and other Cordyceps, proved to have medical ingredients, are also collected for testing as references. It is believed that the specimen selection is justified and objective. Those specimens are listed in Tables 1 and 2. In Table 1, *C. sinensis* and *C. militaris* are collected from different sources. Those specimens from the same source are further assigned to different numbers according to different tissues or fragments for extracting DNA; so that the nature of the sclerotium and the stroma from the same *C. sinensis'* specimen can be identified. The intention of collecting a Saccharomyces cerevisiae as a reference in Table 1 is to determine the reliability of the DNA fragment in polymorphism for Cordyceps after restricted digestion, by referring to the well-known DNA fragment of the Saccharomyces cerevisiae. Table 2, as a comparison to Table 1, is organized to help understanding the nature difference among wild Cordyceps, cultivated Cordyceps, and Cordyceps strains from unknown source.

The target of the testing in accordance with the present invention is the DNA extracted from the specimens in Tables 1 and 2. However, some testing, are invalid due to too short fragments extracted; for example, the 5.8 S rRNA gene in FIG. 1. Also, some testing are discarded, because the extracted fragments are too long to carry effectively amplification of PCR (Polymerase chain reaction). Therefore, the valid testing of the present invention are from those whose extracted fragments are more complete and appropriate in length for 18S rRNA analysis. Further, in each PCR, only limited primers are used for amplification; for example, NS 1 and NS4 in FIG. 1. The gene sequences and position of each primer are listed in Table 3. In the following description, the testing of the present invention will focus at the PCR of the primer pairs, (NS 1+NS4) and (NS3+NS6).

Table 4 lists the DNA fragment sizes in polymorphism for amplification of Table 1 specimens' 18S rRNA gene by PCR using primer pair NS1 and NS4, in which the product was further digested with restriction enzymes Hpa II, Rsa I, Hae III, Sau 3A and Cfo I. As listed, each DNA fragment of the tested *S. cerevisiae* is shown to be the same as the known respective DNA fragment for the *S. cerevisiae*. That is to say that the testing results in DNA fragments for those Cordyceps specimens in Table 4 are all believable. Further, two facts are found among the DNA fragments in Table 4. One is that an identical gene polymorphism (i.e. DNA fragment) is found in all *C. sinensis'* specimens, though from different source. So, that all those *C. sinensis'* specimens belongs to the same species has been proved. Another is that the *C. sinensis* is originated from a single gene, for the founding that the stroma and the sclerotium of the same *C. sinensis'* specimen oppose the same DNA fragment. Yet, in Table 4, it is determine to give up the testing by restriction enzyme Sau3A, for the fact in Table 4 that the restriction enzyme Sau3A cannot digest *C. militaris* (so, no DNA fragment is formed).

Table 5 lists the DNA fragment sizes in polymorphism for amplification of Table 2 specimens' 18S rRNA gene by PCR using primer pair NS1 and NS4, in which the product was further digested with restriction enzymes Hpa II, Rsa I, Hae III, Sau 3A and Cfo I. By comparing Table 5 with Table 4, it is found that only the Cordyceps numbered ATCC 36337 among all fungi of Table 5 carries the same DNA fragment as that for *C. sinensis* of Table 4. Therefore, the ATCC 36337 Cordyceps is proved to originate from the same species as *C. sinensis* does. In addition, it is also found that the polymorphism obtained from digested products by the restriction enzymes Hpa II, Rsa I and Hae III is not sufficient to distinguish the DNA fragments for ATCC 36337 and other specimens. Only the polymorphism obtained from digested products by the restriction enzyme Cfo I can be used to carry the distinguishing. Therefore, in all following testing, the restriction enzyme Cfo I is the only one used to digest the products.

Table 6 lists the DNA fragment sizes in polymorphism for amplification of Table 1 specimens' 18S rRNA gene by PCR using primer pair NS3 and NS6, in which the product was further digested with restriction enzyme Cfo I. Table 7 lists the DNA fragment sizes in polymorphism for amplification of Table 2 specimens' 18S rRNA gene by PCR using primer pair NS3 and NS6, in which the product was further digested with restriction enzyme Cfo I. From Table 5, it is proved that the polymorphism obtained from digested products by the restriction enzyme Cfo I can be used to distinguish accurately wild *C. sinensis'* specimens (numbered Cs7528A1, Cs7528A2, Cs7528JF, Cs7528JH, Cs7528Jt, Cs1014df, and Cs1014db) from other Cordyceps. However, the founding that the ATCC36337 opposes the nature of a genuine *C. sinensis* can't be further confirmed by the testing results from a primer pair NS1 and NS4 in Tables 4 and 5. Therefore, in Tables 6 and 7, the primer pair NS3 and NS6 are used to amplify the 18S rRNA gene, and the PCR product is further digested with Cfo I. By investigating the digested DNA fragments, it is found that all wild *C. sinensis* have the same DNA fragment, as shown in Table 6. Further evidence from Table 4, it is then confirmed that all wild *C. sinensis* belong to the same species. On the other hand, in Table 7, the digested DNA fragment of the ATCC36337 by Cfo I is not the same as that of the wild *C. sinensis*. However, the DNA fragments for *C. militaris* of Table 7 (ATCC26848) and for *C. militaris* of Table 6 (Cm824a and LM1207f) are the same. This finding explains that the ATCC36337 is not a pure *C. sinensis*. Therefore, it is concluded that the difference in DNA fragment among *C. sinensis* and other Cordyceps can be quickly and accurately located by applying the polymorphism of the digested product with restriction enzyme Cfo I after using primer pair NS3 and NS6 in PCR. Hence, the method for distinguishing *C. sinensis* in accordance with the present invention can then become a strong reference to identifying the nature of *C. sinensis*.

While processing the PCR in the testing according to the present invention, reaction condition at each step is: to heat the target DNA at 98° C. for 2 minutes to reach the initial transformation stage, then to perform transforming reaction at 95° C. for 45 seconds, to refine at 95° C. for another 45 seconds, and then to reheat to 72° C. for 2-minute amplification; to repeat all above procedures 35 times; and, finally, to amplify again at 72° C. for 10 minutes.

In summary, the present invention provides an objective distinguishing method for *C. sinensis*, other than the conventional classification methodologies by configuration, by physiology, or by biochemistry. Therefore, by applying the distinguishing method of the present invention, the conventional obscurity in classifying the *C. sinensis* and other Cordyceps is then resolved.

While the present invention has been particularly shown and described with reference to preferred embodiments, it will be understood by those skilled in the art that various changes in form and detail may be without departing from the spirit and scope of the present invention.

TABLE 1

The source and collection number of Cordyceps specimens in this study.

| Species | Collection No. | Tissue used to prepare DNA | Source |
|---|---|---|---|
| *Cordyceps sinensis* | Cs7528A1 | Sclerotium | Collected in Tibet, China |
| *C. sinensis* | Cs7528A2 | Stroma | Collected in Tibet, China |
| *C. sinensis* | Cs7528JF | Stroma | Purchased at Chinese drug store in Taipei |
| *C. sinensis* | Cs7528Jh | Sclerotium (head) | Purchased at Chinese drug store in Taipei |
| *C. sinensi* | Cs7528Jt | Sclerotium (tail) | Purchased at Chinese drug store in Taipei |
| *C. sinensis* | Cs1014df | Stroma | Obtained from Nantong Tonghui edible funguses trading center of Jiangsu, China |
| *C. sinensis* | Cs1014db | Sclerotium | Obtained from Nantong Tonghui edible funguses trading center of Jiangsu, China |
| *C. militaris* | Cm824a | Stroma | Purchased at Chinese drug store in Taipei |
| *C. militaris* | LM1207f | Stroma | Obtained from Sericulture Science Research Institute of Jilin, China |
| *Saccharomyces cerevisiae* | Y824a | Cells | This Laboratory |

TABLE 2

The collection number of Cordyceps strains in this study.

| Species | Collection No. | Source |
|---|---|---|
| *Cordyceps memorabilis* | ATCC 36743 | American Type Culture Collection, U.S.A. |
| *C. militaris* | ATCC 26848 | American Type Culture Collection, U.S.A. |
| *C. ophioglossoides* | ATCC 36865 | American Type Culture Collection, U.S.A. |
| Cordyceps sp. | ATCC 36337 | American Type Culture Collection, U.S.A. |
| *C. sinensis* | CCRC 36421 | Culture Collection & Research Center, Hsinchu, Taiwan. |
| *Phytocordyceps ninchukispora* | CCRC 31900 | Culture Collection & Research Center, Hsinchu, Taiwan. |
| *Aspergillus terreus* | 686 | This laboratory |
| *Ganoderma lucidum* | 950524 | This laboratory |

TABLE 3

| Primer designation | Primer sequences | Position |
|---|---|---|
| N S 1 | GTAGTCATATGCTTGTCTC | 18S rDNA 1-19 |
| N S 3 | GCAAGTGTGGTGCCAGCAGCC | 18S rDNA 553-573 |
| N S 4 | CTTCCGTCAATTCCTTTAAG | 18S rDNA 1131-1150 |
| N S 5 | AACTTAAAGGAATTGACGGAAG | 18 S rDNA 1129-1150 |
| N S 6 | GCATCACAGACCTGTTATTGCCTC | 18 S rDNA 1413-1436 |

TABLE 4

| | Restriction enzyme | | | | |
|---|---|---|---|---|---|
| Collection No. | Hpa II (C↓CGG) | Rsa I (GT↓AC) | Hae III (GG↓CC) | Sau 3A (↓GATC) | Cfo I (GCG↓C) |
| | Restriction fragment size | | | | |
| *C. sinensis* Cs7528A1 | 500, 290, 170, 100, 60 | 517, 410, 180, 60 | 400, 350, 270 | 900, 242, 140 | 400, 350, 270, 150 |

TABLE 4-continued

| | Restriction enzyme | | | | |
|---|---|---|---|---|---|
| Collection No. | Hpa II (C ↓ CGG) | Rsa I (GT ↓ AC) | Hae III (GG ↓ CC) | Sau 3A (↓ GATC) | Cfo I (GCG ↓ C) |
| Cs7528A2 | 500, 290, 170, 100, 60 | 517, 410, 180, 60 | 400, 350, 270 | 900, 242, 140 | 400, 350, 270, 150 |
| Cs7528Jf | 500, 290, 170, 100, 60 | 517, 410, 180, 60 | 400, 350, 270 | 900, 242, 140 | 400, 350, 270, 150 |
| Cs7528Jh | 500, 290, 170, 100, 60 | 517, 410, 180, 60 | 400, 350, 270 | 900, 242, 140 | 400, 350, 270, 150 |
| Cs7528Jt | 500, 290, 170, 100, 60 | 517, 410, 180, 60 | 400, 350, 270 | 900, 242, 140 | 400, 350, 270, 150 |
| Cs1014df | 500, 290, 170, 100, 60 | 517, 410, 180,60 | 400, 350, 270 | 900, 242, 140 | 400, 350, 270, 150 |
| Cs1014db | 500, 290, 170, 100, 60 | 517, 410, 180, 60 | 400, 350, 270 | 900, 242, 140 | 400, 350, 270, 150 |
| *C. militaris* Cm824a | 500, 290, 100 | 677, 410, 60 | 400, 350, 270, 60 | 1000 | 750, 260, 160 |
| LM1207f | 500, 290, 100 | 677, 410, 60 | 400, 350, 270, 60 | 1000 | 750, 260, 160 |
| *S. cerevisiae* Y824a | 520, 390, 300 | 520, 190 | 653, 290, 170 | 1000, 150 | 750, 430 |

TABLE 5

| | Restriction enzyme | | | |
|---|---|---|---|---|
| Collection No. | Hpa II (C ↓ CGG) | Rsa I (GT ↓ CC) | Hae III (GG ↓ CC) | Cfo I (GCG ↓ C) |
| | Restriction Fragment Size | | | |
| *C. memorabilis* ATCC 36743 | 500, 290, 100 | 517, 410, 180, 60 | 400, 350, 270 | 750, 260, 160 |
| *C. militaris* ATCC 26848 | 500, 290, 100 | 677, 410, 60 | 400, 350, 270 | 750, 260, 160 |
| *C. ophioglossoides* ATCC 36865 | 500, 290, 100 | 517, 410, 180, 60 | 400, 350, 270 | 750, 260, 160 |
| Cordyceps. sp. ATCC 36337 | 500, 290, 100 | 517, 410, 180, 60 | 400, 350, 270 | 400, 350, 270, 150 |
| *C. sinensis* CCRC 36421 | 500, 290, 100 | 517, 410, 180, 60 | 400, 350, 270 | 750, 260, 160 |
| *P. ninchukispora* CCRC 31900 | 500, 290, 100 | 517, 410, 180, 60 | 400, 350, 270 | 750, 260, 160 |
| *A. terreus* 686 | 500, 290, 100 60 | 517, 410, 180, 60 | 400, 350, 270 | 750, 260, 150 |
| *G. lucidum* 950524 | 500, 290, 170, 100, 80 | 517, 410, 190, 50 | 400, 350, 270 100 | 750, 260, 150 |

TABLE 6

| Collection No. | PCR product size | Cfo I digested restriction fragment size |
|---|---|---|
| *C. sinensis* | | |
| Cs7528A1 | 920 | 570, 300, 50 |
| Cs7528A2 | 920 | 570, 300, 50 |
| Cs7528Jf | 920 | 570, 300, 50 |
| Cs7528Jh | 920 | 570, 300, 50 |
| Cs7528Jt | 920 | 570, 300, 50 |
| Cs1014df | 920 | 570, 300, 50 |
| Cs1014db | 920 | 570, 300, 50 |
| *C. militaris* | | |
| Cm824a | 1300 | 630, 310, 184, 90, 50 |
| LM1207f | 1300 | 630, 310, 184, 90, 50 |
| *S. cerevisiae* Y824a | 920 | 920 |

TABLE 7

| Collection No. | PCR product size | Cfo I digested restriction fragment size |
|---|---|---|
| *C. memorabilis* ATCC 36743 | 920 | 920 |
| *C. militaris* ATCC 26848 | 1300 | 630, 310, 184, 90, 50 |
| *C. ophioglossoides* ATCC 36865 | 920 | 920 |

TABLE 7-continued

| Collection No. | PCR product size | Cfo I digested restriction fragment size |
|---|---|---|
| Cordyceps sp. ATCC 36337 | 920 | 630, 300 |
| C. sinensis CCRC 36421 | 920 | 920 |
| Phytocordyceps ninchukispora | 1300 | 830, 320, 150 |
| CCRC 31900 Aspergillus terreus 686 | 1300 | 920 |
| Ganoderma lucidum 950524 | 920 | 920 |

We claim:

1. A method for identifying *Cordyceps sinensis*, which comprises extracting DNA from a Cordyceps specimen;

amplifying the DNA encoding 18S rRNA by PCR wherein the DNA contains a restriction fragment length polymorphism and wherein the PCR is performed using primer pair NS3 and NS6;

digesting the amplified DNA fragments with restriction enzyme Cfo I;

determining the restriction fragment lengths of the digested DNA; and identifying the specimen as *Cordyceps sinensis* by the presence of polymorphic restriction fragments lengths of 570bp, 300bp and/or 50bp.

2. The method for identifying *Cordyceps sinensis* of claim 1, wherein said PCR is performed using the following reaction conditions:

initial transformation 98° C. for 2 minutes;

transformation, 95° C. for 45 seconds;

refining, 52° C. for 45 seconds;

amplifying, 72° C. for 2 minutes;

repeating transformation, refining and amplification for 35 cycles; and final amplification, 72° C. for 10 minutes.

* * * * *

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:primer NS1

<400> SEQUENCE: 1
gtagtcatat gcttgtctc                                              19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer NS3

<400> SEQUENCE: 2
gcaagtctgg tgccagcagc c                                           21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer NS4

<400> SEQUENCE: 3
cttccgtcaa ttcctttaag                                             20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:primer NS5

<400> SEQUENCE: 4
aacttaaagg aattgacgga ag                                          22

<210> SEQ ID NO 5
<211> LENGTH: 24
<212> TYPE: DNA
```

```
<213> ORGANISM: Artificial Sequence
<220> FEATURE:
<223> OTHER INFORMATION: Description of Artificial Sequence:primer NS6

<400> SEQUENCE: 5
gcatcacaga cctgttattg cctc                                            24
```